United States Patent
Wolf

(10) Patent No.: US 6,670,481 B2
(45) Date of Patent: Dec. 30, 2003

(54) OXIRANECARBOXYLIC ACIDS FOR THE TREATMENT OF DIABETES

(75) Inventor: Horst P. O. Wolf, Allensbach (DE)

(73) Assignee: Medicone AG Gesellschaft fur Molekularbiologische Kardiologie, Planegg/Martinsried (DE)

( * ) Notice: Subject to any disclaimer, the term of this patent is extended or adjusted under 35 U.S.C. 154(b) by 18 days.

(21) Appl. No.: 10/173,444

(22) Filed: Jun. 18, 2002

(65) Prior Publication Data

US 2002/0198382 A1 Dec. 26, 2002

Related U.S. Application Data

(62) Division of application No. 09/367,383, filed as application No. PCT/EP98/00611 on Feb. 5, 1998, now Pat. No. 6,479,676.

(30) Foreign Application Priority Data

Feb. 14, 1997 (DE) .......................... 197 05 718

(51) Int. Cl.⁷ ............................................ C07D 271/10
(52) U.S. Cl. ......................................................... 548/144
(58) Field of Search ........................... 549/6, 332, 429, 549/512, 518; 514/385, 365, 372, 406, 403, 408, 444, 422, 449, 475; 548/144, 206, 517, 356.1, 361.1, 373.1

(56) References Cited

U.S. PATENT DOCUMENTS

| 4,324,796 A | 4/1982 | Eistetter et al. |
|---|---|---|
| 4,337,267 A | 6/1982 | Eistetter et al. |
| 4,788,304 A | 11/1988 | Marshall et al. |
| 4,788,306 A | 11/1988 | Schiehser et al. |
| 4,946,866 A | 8/1990 | Wolf et al. |
| 5,447,954 A | 9/1995 | Gribble et al. |
| 6,013,666 A * | 1/2000 | Jew et al. .................... 514/475 |

FOREIGN PATENT DOCUMENTS

| JP | 57-501233 | 7/1982 |
|---|---|---|
| JP | 2000-513373 | 10/2000 |
| WO | WO 83/00334 | 2/1983 |
| WO | 98/00422 | * 1/1998 |

OTHER PUBLICATIONS

Daniel Colombani, Synthesis of Methacrylic–type . . . , Tetrahedron , vol 53, No 7 1997.*

* cited by examiner

Primary Examiner—Alan L. Rotman
Assistant Examiner—Rita Desai
(74) Attorney, Agent, or Firm—Clark & Elbing LLP

(57) ABSTRACT

The invention relates to novel arylalkyl- or aryloxyalkyl-substituted oxiranecarboxylic acids of the general formula I:

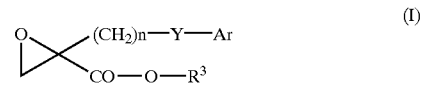

in which Ar, R³, Y and n are as defined in the description, and also to medicaments comprising them and to their use for the treatment and prophylaxis of the disorders mentioned in claim 4 which are caused by disturbances of glucose and/or lipid metabolism, such as, for example, diabetes type 2 and other insulin-resistant conditions.

15 Claims, No Drawings

OXIRANECARBOXYLIC ACIDS FOR THE TREATMENT OF DIABETES

This application is a divisional of U.S. Ser. No. 09/367,383, filed Aug. 13, 1999, now U.S. Pat. No. 6,479,676 B1, which is the 371 National Phase of International Application No. PCT/EP98/00611, filed Feb. 5, 1998, which claims priority from German Application DE 197 05 718.7, filed Feb. 14, 1997, all hereby incorporated by reference.

AREA OF APPLICATION OF THE INVENTION

The invention relates to novel arylalkyl- or aryloxylalkyl-substituted oxiranecarboxylic acids, to processes for their preparation, to their use and to medicaments comprising them.

PRIOR ART

EP 0 046 590 describes hypoglycaemically and hypoketonaemically active phen(alk)oxy-substituted oxiranecarboxylic acids and esters thereof of the general formula A:

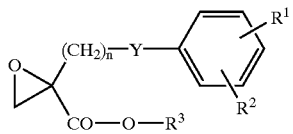

(A)

in which
R$^1$ is a hydrogen atom, a halogen atom, a 1–4 C-lower alkyl group, a 1–4 C-lower alkoxy group, a nitro group or a trifluoromethyl group,
R$^2$ has one of the meanings of R$^1$,
R$^3$ is a hydrogen atom or a 1–4 C-lower alkyl group,
Y is the grouping —O—(CH$_2$)$_m$—,
m is 0 or an integer from 1 to 4 and
n is an integer from 1 to 8,
where the sum of m and n is an integer from 2 to 8, and the salts of the carboxylic acids.

EP 0 231 367 B1 describes the use of the compounds of the general formula A for the prevention and/or treatment of disorders which are caused by an elevated concentration of cholesterol and/or triglyceride in the organism.

DE-A 4 340 879 A1 describes the use of the compounds of the general formula A in the prevention and/or treatment of cardiac insufficiency.

DE-A 3 032 668 describes, inter alia, non-aromatic cycloalkyl(alk)oxy-substituted oxiranecarboxylic acids.

EP 0 283 168 describes phenylalkyl- and phenoxyalkyloxiranecarboxylic acids and esters thereof having 1–2 fluorine substituents in the alkyl chain which are said to act as inhibitors of fatty acid oxidation with a low potential to cause damage to cardiac muscle function.

DESCRIPTION OF THE INVENTION

The invention provides novel arylalkyl- or aryloxyalkyl-substituted oxiranecarboxylic acids or pharmacologically acceptable salts thereof of the general formula I

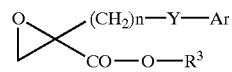

(I)

in which
Ar is a substituted phenyl radical

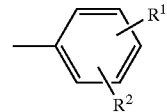

R$^1$ is a hydrogen atom, a halogen atom or a 1–4 C-lower alkyl group,
R$^2$ is one of the groups

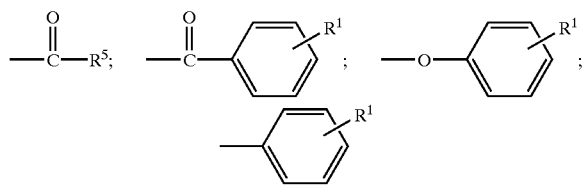

or a fully or predominantly fluorine-substituted 1–3 C-alkoxy group,
R$^3$ is a hydrogen atom or a 1–4 C-lower alkyl group,
R$^4$ is a hydrogen atom, a 1–4 C-lower alkyl group, an optionally fully or predominantly fluorine-substituted 1–3 C-alkoxy group or a halogen atom,
R$^5$ is a 1–4 C-lower alkyl group,
Y is the grouping —O— or —CH$_2$—,
n is an integer from 2 to 8 and
Het is a heterocyclic ring, which preferably has 5 members and is selected from the group consisting of thiophene, thiazole, isothiazole, pyrrole and, particularly preferably, pyrazole, and which may carry 1 or 2 identical or different substituents R$^1$,
where the chain —(CH$_2$)$_n$— may optionally be interrupted by a —CH(CH$_3$)— or —C(CH$_3$)$_2$— unit, and
the salts of the corresponding carboxylic acids (R$_3$=H).

The 1–4 C-lower alkyl radicals can be straight-chain or branched. Straight-chain alkyl radicals are, for example, the methyl, ethyl, n-propyl and the butyl radical, of which those having 1 to 2 carbon atoms are preferred. Branched alkyl radicals are, for example, the isopropyl, isobutyl and the sec-butyl radical, of which that having 3 carbon atoms is preferred. Suitable alkyl radicals of lower alkoxy groups are both straight-chain and branched lower alkyl groups. A preferred lower alkyl group is the methoxy group. Suitable alkyl radicals in acyl groups are both straight-chain and branched lower alkyl groups, of which the methyl group and the tert-butyl group are preferred.

Halogen atoms are fluorine, chlorine and bromine atoms, of which fluorine and, in particular, chlorine, are preferred.

In the substituted phenyl radicals Ar, the substituents R$^1$ and R$^2$ are preferably in the m- or p-position and R$^1$ is preferably a hydrogen atom.

Among the fully or predominantly fluorine-substituted 1–3—C-alkoxy groups, preference is given to the trifluoromethoxy, the 2,2,2-trifluoroethoxy, the 1,1,2,2-tetrafluoroethoxy group and in particular to the difluoromethoxy group.

Suitable salts are salts with inorganic and organic bases. Pharmacologically unacceptable salts are converted, by methods known per se, into pharmacologically, i.e. biologically, acceptable salts, which are preferred from among the salts according to the invention. Suitable cations for use for salt formation are, in particular, the cations of the alkali metals, alkaline earth metals or noble metals;

however, it is also possible to use the corresponding cations of organic nitrogen bases, such as amines, aminoalcohols, amino sugars, basic amino acids, etc.

Examples which may be mentioned are salts of lithium, sodium, potassium, magnesium, calcium, aluminium, ethylenediamine, dimethylamine, diethylamine, morpholine, piperidine, piperazine, N-lower alkyl piperazine (for example N-methylpiperazine), methycyclohexylamine, benzylamine, ethanolamine, diethanolamine, triethanolamine, tris-(hydroxymethyl)-aminomethane, 2-amino-2-methylpropanol, 2-amino-2-methyl-1,3-propanediol, glucamine, N-methylglucamine, glucosamine, N-methylglucosamine, lysine, ornithine, arginine, quinoline.

The arylalkyl- or aryloxyalkyloxiranecarboxylic acids of the general formula I according to the invention have a chiral centre. Accordingly, the invention includes both the racemates and the enantiomers and mixtures thereof. For racemate separation of the carboxylic acids, particular preference is given to using salts with optically active bases, such as cinchonidine or dehydroabietylamine.

The compounds according to the invention have useful pharmacological properties which make them. They have hypoglycaemic and lipid-lowering action and improve the efficacy of insulin in the treatment of insulin-resistant conditions, such as, for example, in the case of metabolic syndrome and, in particular, diabetes type 2.

They are superior to the known oxiranecarboxylic acids of the prior art in the following manner:

a) they are distinguished by a therapeutic index which is significantly better under certain conditions in the manner that the increases of liver enzymes (transaminases) which occur in individual type 2-diabetics occur to a considerably lesser extent, if at all, b) they have superior action with respect to increasing the effect of insulin in insulin-resistant conditions, c) they are metabolized more quickly and do not form any long-lasting metabolites.

Owing to their advantageous and superior efficacy, the compounds of the general formula I according to the invention and the pharmacologically acceptable salts are suitable for the treatment and prophylaxis of disorders which are caused by disturbances of glucose and lipid metabolism, in human and veterinary medicine.

They are employed, for example, for treating prediabetic conditions; for the treatment and prevention of the manifestation of diabetes type 2 and of all pathological conditions which are associated with pathological insulin resistance; for the treatment and prevention of the manifestation of all pathological conditions with pathologically elevated production of ketone bodies; for the treatment and prevention of the manifestation of all pathological conditions which are caused by elevated cholesterol and/or triglyceride concentrations in the blood (hyperlipidaemia, arteriosclerosis, coronary heart disease).

The invention also provides the compounds according to the invention for use in the treatment and prophylaxis of the disorders mentioned.

The invention furthermore provides medicaments comprising one or more arylalkyl- or aryloxyalkyloxiranecarboxylic acids of the general formula I

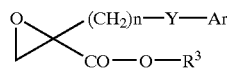

(I)

in which

Ar is a substituted phenyl radical

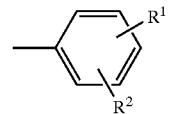

a 1- or 2-naphthyl radical which is substituted by a radical $R^4$ or is a heterocyclic radical Het, $R^1$ is a hydrogen atom, a halogen atom or a 1–4 C-lower alkyl group, $R^2$ is one of the groups

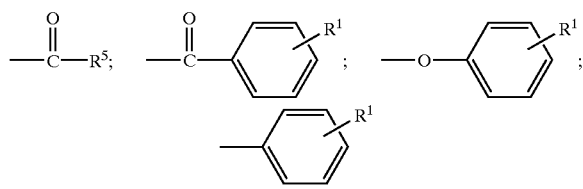

or a fully or predominantly fluorine-substituted 1–3 C-alkoxy group, $R^3$ is a hydrogen atom or a 1–4 C-lower alkyl group, $R^4$ is a hydrogen atom, a 1–4 C-lower alkyl group, an optionally fully or predominantly fluorine-substituted 1–3 C-alkoxy group or a halogen atom, $R^5$ is a 1–4 C-lower alkyl group, Y is the grouping —O— or —$CH_2$—, n is an integer from 2 to 8 and Het is a heterocyclic ring, which preferably has 5 members and is selected from the group consisting of thiophene, thiazole, isothiazole, pyrrole and, particularly preferably, pyrazole, and which may carry 1 or 2 identical or different substituents $R^1$, where the chain —$(CH_2)_n$— may optionally be interrupted by a —$CH(CH_3)$— or —$C(CH_3)_2$— unit, and the pharmacologically acceptable salts of the carboxylic acids ($R^3$=H) with inorganic or organic bases.

Moreover, the invention provides the use of the compounds according to the invention for preparing medicaments for controlling the disorders mentioned.

The medicaments are prepared by processes known per se. As medicaments, the compounds according to the invention are employed either as such or, if appropriate, in combination with suitable pharmaceutical excipients. If the pharmaceutical preparations comprise pharmaceutical excipients in addition to the active compounds, the active compound content of this mixture is from 1 to 95, preferably from 10 to 85% (w/w) of the total mixture. The medicaments are formulated in suitable doses, for example for oral or parenteral (intravenous, intramuscular) administration. The daily dose for oral administration in humans is generally between 0.1 and 30, preferably between 0.3 and 15, in particular between 0.6 and 3 mg/kg of body weight. The dosage for parenteral treatment is between 0.3 and 1 mg of active compound/kg of body weight.

The pharmaceutical preparations preferably comprise the active compounds according to the invention and non-toxic, pharmaceutically acceptable pharmaceutical excipients which are employed as additive or diluent in solid, semi-solid or liquid form or as coating material for example in the form of a capsule, a tablet coating, a bag or another container for the therapeutically active component. An excipient may serve, for example, to mediate the uptake of the medicament by the body, as formulation auxiliary, as sweetener, as taste corrigent, as colorant or as preservative.

In addition to the compounds of the general formula I according to the invention in which the substituents are as defined above, and/or their salts, the pharmaceutical preparations may furthermore, comprise one or more pharmacologically active components of other medicament groups, such as antidiabetics (sulphonamides, sulphonylureas, thiazolidinediones, etc.) or hypolipedemics (nicotinic acid and its derivatives, clofibrate, HMG-CoA reductase inhibitors).

The compounds according to the invention are prepared by processes known per se. Detailed instructions for preparing the principal compound class are described in EP 0046 590, equivalent to Eistetter et al., U.S. Pat. No. 4,337,267, the disclosure of which is incorporated herein by reference.

Here, the compounds of the general formula I are usually obtained in the form of racemic mixtures, which are separated into the enantiomers using known methods. For example, the racemate is converted into diastereomers using an optically active resolving agent, and the diastereomers are subsequently separated by selective crystallization and converted into the corresponding optical isomers. Optically active resolving agents which can be employed are, for example, optically active bases, such as 1- and d-1-phenylethylamine, cinchonidine or d-ephedrine, which are used to prepare salts of the acids of the general formula I, or optically active alcohols, such as borneol or menthol, which are used to prepare esters from the acids of the general formula I. Racemate resolution of the acids using dehydroabiethylamine as salt rormer has been round to be particularly suitable.

The Examples below are intended to illustrate the invention in more detail, without limiting it.

EXAMPLE 1

The compounds of the formula I according to the invention lower the glucose concentration in the blood of rats which have been made insulin-resistant by prolonged fasting. In this action, the said compounds are superior to the active compounds known from the prior art, for example rac-etomoxir (see EP 046 590).

In the Table below, the representative substances which were examined are numbered for identification:

| Number | Name of the compound |
|--------|----------------------|
| 1 | Ethyl 2-(6-(4-chlorophenoxy)hexyl)oxirane-2-carboxylate |
| 2 | Ethyl 2-(6-(4-difluoromethoxyphenoxy)hexyl)oxirane-2-carboxylate |
| 3 | Ethyl 2-(5-(4-difluoromethoxyphenoxy)pentyl)oxirane-2-carboxylate |
| 4 | Ethyl 2-(5-(4-acetylphenoxy)pentyl)oxirane-2-carboxylate |

In Table 1, the following findings are shown:

| | |
|---|---|
| In Column A | The blood glucose-lowering effect of the representative substances in insulin-resistant rats (after 24 hour fasting) 2 hours after oral administration of equimolar doses (100 μmol/kg of body weight) |
| In Column B | The triglyceride-lowering effect of the representative substances in the blood plasma of fed, healthy rats after oral administration of equimolar doses (100 μmol/kg of body weight) for 16 days, 24 hours after the last administration of substance. |
| In Column C | The cholesterol-lowering effect of the representative substances in the blood plasma of fed, healthy rats after oral administration of equimolar doses (100 μmol/kg of body weight) for 16 days, 24 hours after the last administration of substance. |

What is stated are the changes in per cent of the animals which have been treated with substance, compared to control animals which were treated with placebo, calculated from the mean values of in each case 10 individual values.

TABLE 1

| Substance No. | (A) Glucose (%) | (B) Triglycerides (%) | (C) Cholesterol (%) |
|---|---|---|---|
| 1 | −18 | −50 | −15 |
| 2 | −27 | −69 | −13 |
| 3 | −27 | −73 | −26 |
| 4 | −7 | −41 | −8 |

The superiority of the compounds according to the invention compared to the prior art with respect to lowering glucose after fasting, chosen as an experimental model of insulin resistance, is particularly pronounced in the case of the substances No. 2 and 3 in Tab. 1. Taking into account the triglyceride- and cholesterol-lowering effect, substance No. 3 in particular has an effect which is superior to the prior art.

EXAMPLE 2

Table 2 shows the influence of the representative substances on undesirable side effects which have been described in the scientific literature (K. Ratheiser, B. Schneeweiss et al.: Metabolism Clin. Exp. 40 (1991) 1185; H. P. O. Wolf in C. J. Bailey & P. R. Flatt, New antidiabetic drugs, Smith-Gordon, London 1990):

| | |
|---|---|
| In Column A | The transient increase in the activity of the liver enzyme glutamic-pyruvate transaminase (GPT) in the blood plasma after oral administration of equimolar doses of the substances to healthy, fed rats for 16 days, 24 hours after the last administration of substance. |
| In Column B | The increase of the relative weight of the heart (weight of the heart/100 g of body weight) as an indication of cardiac hypertrophy after oral administration of equimolar doses of the substances to healthy, fed rats for 16 days, 24 hours after the last administration of substance. |
| In Column C | The pharmacological safety index, calculated from the lowering of the blood concentrations of glucose + triglycerides + cholesterol in per cent divided by the increase of GPT activity + relative weight of the heart in per cent. |

TABLE 2

| Substance No. | (A) GPT activity (%) | (B) Relative weight of the heart (%) | (C) Safety index (%) |
|---|---|---|---|
| 1 | 8 | 14 | 3.77 |
| 2 | 5 | 14 | 5.74 |
| 3 | 12 | 11 | 5.48 |
| 4 | −9 | −2 | 56 |

The higher the index, the greater the safety of the substance. In this respect, the substance No. 4 is distinguished in that it is particularly superior to the prior art. The substances No. 2 and 3 are likewise superior to the prior art.

EXAMPLE 3

Test Animals

The test animals used were male Sprague-Dawley rats from the SPF breed Ivanovas (Kisslegg, Germany) having a body mass of 255–400 g. The animals were kept in a conventional manner, 4 animals each in cages made of Makrolon (22×38 cm) in a climatized room (21–23 degrees Celcius) with a fixed day/night rhythm (7a.m/7p.m) and a regulated relative atmospheric humidity of 55–60%. The animals received a maintenance diet—Altromin 1320 from Altromin (Lage, Germany)—and water ad libitum.

To determine the effect of the substance on blood glucose, feed was withdrawn 24 hours before the administration of the substance to produce an insulin-resistant condition.

The animals were divided at random in 5 groups of 10 animals each and marked. The substances were administered to the animals in the form of a neutral, aqueous emulsion (1 part by weight of substance+2 parts by weight of Cremophor EL—an emulsifier from BASF AG, Germany—) in a volume of 10 ml/kg of body weight using a stomach tube.

EXAMPLE 4

Preparation of Blood and Serum

To determine the glucose in the blood, 50 μl of blood were collected from the retrobulbular venousplexus 2 hours after the administration of the substance, using a glass capillary, from animals which had been fasting for 24 hours, and the blood was deproteinated in ice-cold perchloric acid (0.66 mol/l). After centrifugation, the glucose was determined in the supernatant using enzymatic standard methods.

To determine the parameters triglycerides, cholesterol and the activity of the glutamic-pyruvic transaminase (GPT), blood plasma was used. The blood plasma was obtained as an erythrocyte-free supernatant 15 minutes after venous blood sampling into heparinized Eppendorf reaction vessels by centrifugation (2×2 minutes at 16,000 rpm in an Eppendorf centrifuge).

EXAMPLE 5

Analytical Methods

Glucose:

Enzymatic test with hexokinase/glucose-6-phosphatase, test combination from Boehringer Mannheim, Germany.

Triglycerides:

Enzymatic test with lipase/glycerokinase, test combination from Boehringer Mannheim, Germany.

Cholesterol:

Enzymatic colour test (CHOD-PAP method), test combination from Boehringer Mannheim, Germany.

GPT:

Kinetic enzyme test, test combination from Boehringer Mannheim, Germany.

Relative weight of the heart:

The animals were killed by decapitation and exsanguination, and the weight of the heart muscle, which had been freed from the right atrium, was determined by weighing and based on 100 g of body. weight.

What is claimed is:

1. A compound of the formula I

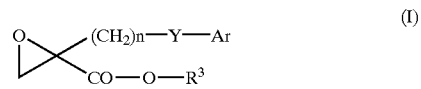

in which

Ar is a heterocyclic radical Het, $R^3$ is a hydrogen atom or a 1–4 C-lower alkyl group, Y is —O— or —$CH_2$—, n is an integer from 2 to 8, Het is a five membered heterocyclic ring, which may carry 1 or 2 identical or different substituents $R^1$, and $R^1$ is a hydrogen atom, a halogen atom, or a 1–4 C-lower alkyl group, where the chain —$(CH_2)_n$— may optionally be interrupted by a —$CH(CH_3)$— or —$C(CH_3)_2$— unit, and the salts of the carboxylic acids ($R^3$=H).

2. The compound of formula I according to claim 1 wherein the heterocyclic ring is selected from the group consisting of thiophene, thiazole, isothiazole, pyrrole and pyrazole.

3. The compound of formula I according to claim 1 wherein the heterocyclic ring is thiophene.

4. The compound of formula I according to claim 1 wherein the heterocyclic ring is thiazole.

5. The compound of formula I according to claim 1 wherein the heterocyclic ring is isothiazole.

6. The compound of formula I according to claim 1 wherein the heterocyclic ring is pyrrole.

7. The compound of formula I according to claim 1 wherein the heterocyclic ring is pyrazole.

8. A pharmaceutical preparation comprising one or more compounds of formula I according to claim 1 together with a pharmaceutically acceptable excipient and/or auxiliary.

9. The pharmaceutical preparation according to claim 8 wherein the heterocyclic radical Het in formula I is selected from the group consisting of thiophene, thiazole, isothiazole, pyrrole and pyrazole.

10. A method for treating disorders caused by disturbances of glucose and/or lipid metabolism comprising the steps of:

a) providing the compound or mixture of compounds of formula I according to claim 1; and b) administering an effective amount of the compound or mixture of compounds to an animal in need of such a treatment.

11. The method according to claim 10 wherein the heterocyclic radical Het in formula I is selected from the group consisting of thiophene, thiazole, isothiazole, pyrrole and pyrazole.

12. The method of claim 11 wherein the disorder is elevated glucose.

13. The method of claim 11 wherein the disorder is elevated triglyceride.

14. The method of claim 11 wherein the disorder is elevated cholesterol.

15. The method of claim 14 wherein the disorder is selected from the group consisting of pathological glucose tolerance, prediabetes, diabetes type 2, conditions with insulin resistance, conditions with pathologically elevated production of ketone bodies, hyperlipidaemia, arteriosclerosis and coronary heart disease.

* * * * *